United States Patent
Kuo et al.

(10) Patent No.: US 8,046,175 B2
(45) Date of Patent: Oct. 25, 2011

(54) ANALYTICAL STRIP READING APPARATUS AND THE ANALYICAL STRIP USED THEREIN

(75) Inventors: Chien-Chih Kuo, Hsinchu (TW); Wen-Pin Hsieh, Hsinchu (TW); Ching-Tai Tseng, Hsinchu (TW)

(73) Assignee: Actherm Inc, Hsinchu (TW)

( * ) Notice: Subject to any disclaimer, the term of this patent is extended or adjusted under 35 U.S.C. 154(b) by 407 days.

(21) Appl. No.: 12/350,467

(22) Filed: Jan. 8, 2009

(65) Prior Publication Data

US 2010/0094564 A1    Apr. 15, 2010

(30) Foreign Application Priority Data

Oct. 13, 2008  (WO) ................ PCT/CN2008/001724
Dec. 5, 2008   (WO) ................ PCT/CN2008/001978

(51) Int. Cl.
*C12Q 1/00*   (2006.01)
*G12B 13/00*  (2006.01)
*G01N 35/00*  (2006.01)
*G06F 19/00*  (2011.01)

(52) U.S. Cl. ........ 702/19; 73/1.02; 235/462.01; 422/63; 436/43; 600/300

(58) Field of Classification Search ................. 73/1.01, 73/1.02, 53.01, 432.1, 863, 865.8; 235/435, 235/439, 454, 462.01; 283/72, 74, 81; 356/39, 356/51, 244; 422/44, 50, 63, 119, 500; 436/43, 436/46, 47; 600/300; 702/1, 13, 22, 127, 702/187, 189, 19
See application file for complete search history.

(56) References Cited

U.S. PATENT DOCUMENTS

| | | | |
|---|---|---|---|
| 3,907,503 A * | 9/1975 | Betts et al. ...................... 422/67 |
| 4,325,910 A * | 4/1982 | Jordan ............................ 422/64 |
| 4,608,231 A | 8/1986 | Witty et al. |
| 4,675,299 A | 6/1987 | Witty et al. |
| 4,678,752 A | 7/1987 | Thorne et al. |
| 4,873,633 A | 10/1989 | Mezei et al. |
| 5,126,952 A | 6/1992 | Kildal-Brandt et al. |
| 5,128,105 A | 7/1992 | Berthold |
| 5,229,074 A | 7/1993 | Heath et al. |
| 5,281,395 A | 1/1994 | Markart et al. |
| 5,316,726 A | 5/1994 | Babson et al. |
| 5,374,395 A | 12/1994 | Robinson et al. |
| 5,445,147 A | 8/1995 | Schoendorfer et al. |
| 5,798,035 A | 8/1998 | Kirk et al. |
| 5,822,071 A | 10/1998 | Dosmann et al. |
| 5,885,529 A | 3/1999 | Babson et al. |
| 5,885,530 A | 3/1999 | Babson et al. |
| 5,902,982 A | 5/1999 | Lappe |
| 5,929,422 A | 7/1999 | Lappe |
| 6,036,092 A | 3/2000 | Lappe |

(Continued)

FOREIGN PATENT DOCUMENTS

CN  1536522 A  10/2004

(Continued)

*Primary Examiner* — Edward Cosimano
(74) *Attorney, Agent, or Firm* — Ming Chow Sinorica, LLC

(57) ABSTRACT

The invention discloses an analytical strip reading apparatus and the analytical strip used therein. The analytical strip reading apparatus comprises a housing, a monitor, a delivering device, an optical reader, a reaction signal reader and a control module. The analytical strip comprises at least one optically readable pattern which comprises identification information of the analytical strip.

18 Claims, 5 Drawing Sheets

U.S. PATENT DOCUMENTS

| | | | |
|---|---|---|---|
| 6,097,025 | A | 8/2000 | Modlin et al. |
| 6,120,733 | A | 9/2000 | Goodman |
| RE37,194 | E | 5/2001 | Kirk et al. |
| 6,269,313 | B1 | 7/2001 | Givens et al. |
| 6,319,668 | B1 | 11/2001 | Nova et al. |
| 6,656,428 | B1 | 12/2003 | Clark et al. |
| RE38,509 | E | 5/2004 | Lappe |
| 6,770,487 | B2 | 8/2004 | Crosby |
| 6,780,645 | B2 * | 8/2004 | Hayter et al. ............... 436/8 |
| 6,830,731 | B1 | 12/2004 | Buechler et al. |
| 6,867,051 | B1 | 3/2005 | Anderson et al. |
| 6,869,570 | B2 * | 3/2005 | Wardlaw ............... 422/82.05 |
| 7,064,823 | B2 | 6/2006 | Roche et al. |
| 7,368,281 | B2 | 5/2008 | Mozdy et al. |
| 7,390,458 | B2 | 6/2008 | Burow et al. |
| 7,416,700 | B2 | 8/2008 | Buechler et al. |
| 7,427,380 | B2 | 9/2008 | McNeil et al. |
| 7,604,721 | B2 * | 10/2009 | Groll et al. ............ 204/403.01 |
| 7,645,373 | B2 * | 1/2010 | Groll et al. ............... 205/777.5 |
| 7,645,421 | B2 * | 1/2010 | Groll ............... 422/501 |
| 7,718,439 | B2 * | 5/2010 | Groll ............... 436/149 |
| 7,784,678 | B2 * | 8/2010 | Kuo et al. ............ 235/375 |
| 7,955,856 | B2 * | 6/2011 | Neel et al. ............ 436/149 |
| 2002/0055178 | A1 * | 5/2002 | Wardlaw ............... 436/165 |
| 2003/0124738 | A1 * | 7/2003 | Crosby ............... 436/514 |
| 2003/0157723 | A1 * | 8/2003 | Smith et al. ............ 436/43 |
| 2004/0038411 | A1 * | 2/2004 | Hayter et al. ............ 436/14 |
| 2004/0162988 | A1 | 8/2004 | Harper |
| 2005/0016846 | A1 * | 1/2005 | Groll et al. ............ 204/403.03 |
| 2005/0019805 | A1 * | 1/2005 | Groll ............... 435/6 |
| 2005/0019953 | A1 * | 1/2005 | Groll ............... 436/514 |
| 2005/0161345 | A1 * | 7/2005 | Groll et al. ............ 205/792 |
| 2006/0189895 | A1 * | 8/2006 | Neel et al. ............ 600/584 |
| 2006/0216832 | A1 * | 9/2006 | Nishikawa et al. ........... 436/514 |
| 2007/0110615 | A1 * | 5/2007 | Neel et al. ............ 422/57 |
| 2010/0111764 | A1 * | 5/2010 | Groll ............... 422/58 |
| 2010/0140341 | A1 * | 6/2010 | Kuo et al. ............ 235/375 |

FOREIGN PATENT DOCUMENTS

| | | |
|---|---|---|
| CN | 2739639 | 11/2005 |
| CN | 201005780 | 1/2008 |
| CN | 201107317 Y | 8/2008 |
| CN | 201117004 | 9/2008 |
| EP | 0299521 A2 | 1/1989 |
| EP | 0485831 A1 | 5/1992 |
| WO | WO2007096191 A1 | 8/2007 |

* cited by examiner

ANALYTICAL STRIP READING APPARATUS AND THE ANALYICAL STRIP USED THEREIN

BACKGROUND OF THE INVENTION

1. Technical Field

The present invention relates to a reading apparatus, and more particularly, to a reading apparatus for biological analytical strips.

2. Description of Related Art

With the progress of the medical industry and the electronic industry, a variety of detecting apparatuses, such as electronic ear thermometers and electronic sphygmomanometers, have been developed for family medical care. Among all biochemical or immunological detecting apparatuses, the more common ones are those for detecting blood glucose, uric acid or total cholesterol. Such kinds of detecting systems can be divided into optical systems and electrochemical systems, as distinguished by the reaction signals involved. The electrochemical systems are more frequently used.

Since detection of different test samples requires the use of different substances as reagents, it is necessary to use different analytical strips in different types of tests. For example, blood glucose analytical strips are needed in blood glucose tests while uric acid analytical strips are called for in uric acid tests. In addition, in order to ensure the reliability of test results, only analytical strips that have not passed their expiration dates can be used. On the other hand, a conventional detecting machine typically uses an additional calibration chip to store such calibration information as the types, lot numbers and expiration dates of analytical strips. Prior to testing, a calibration chip corresponding to the type and lot number of the analytical strip to be used is inserted into the socket of the detecting machine, allowing the detecting machine to not only read the calibration information from the calibration chip, but also display the type, the lot number and the expiration date of the analytical strip, so that a user can confirm for himself/herself whether or not the calibration information displayed on the machine, such as the type and the lot number, belongs to the analytical strip intended to be used, and whether or not the analytical strip has passed the expiration date. In addition, the calibration chip may also contain calibration information regarding detection values of analytical strips bearing the same lot number. Therefore, to ensure accurate test results, the analytical strip in use must have the same lot number as that of the calibration chip. While using the detecting machine described above, the user has to verify the type, the lot number and the expiration date of analytical strips on his/her own. Hence, in case of an inadvertent mistake, the user may erroneously use analytical strips that belong to a wrong type, have passed their expiration dates or bear a different lot number from that of the calibration ship, thereby compromising the accuracy of test results.

Furthermore, most of the commercially available analytical strips need to be inserted into or removed from the detecting machine manually. However, it usually happened that the user may accidentally come into contact with the analytical strips during the manual operation, thereby contaminate the specimen and ruin the detection.

BRIEF SUMMARY OF THE INVENTION

In order to solve the aforementioned problems, the present invention provides an analytical strip reading apparatus for reading a reaction signal emitted from an analytical strip. The analytical strip reading apparatus comprises a housing, a monitor, a delivering device, an optical reader, a reaction signal reader and a control module. The analytical strip for the reading apparatus has at least one reaction zone for presenting the reaction signal and at least one optically readable pattern with identification information of the analytical strip. The monitor is provided on the housing for displaying an analysis result. The delivering device is configured for supporting the analytical strip and moving the analytical strip along a preset route so as to deliver the analytical strip into or out of the housing. The optical reader is configured for reading identicication information contained in the optically readable pattern of the analytical strip, wherein the identicication information essentially comprises a type, a lot number and an expiration date of the analytical strip as well as reagent calibration data corresponding to the lot number. The reaction signal reader is configured for acquiring the reaction signal emitted from the analytical strip. In addition, the control module comprises a mother board and a firmware device attached to the mother board. The firmware device includes a database sub-module and a processing sub-module, wherein the database sub-module is configured for algorithms corresponding to various types of analytical strips, and the processing sub-module is configured for retrieving the algorithm stored in the database sub-module corresponding to the type of the analytical strip, combining the reagent calibration data corresponding to the lot number of the analytical strip, and comparing the reaction signal from the analytical strip, so as to come out an analysis result of the assay.

Therefore, a principal objective of the present invention is to provide an analytical strip reading apparatus, wherein an optical reader is provided and configured to read identification information contained in an optically readable pattern of an analytical strip, thereby enabling automatic comparison and verification of a type, a lot number and an expiration date of the analytical strip and reagent calibration data corresponding to the lot number. Thus, the incorrect operation or improper analytical strips can be prevented to ensure the reliability of analysis results.

Another objective of the present invention is to provide an analytical strip reading apparatus comprising a delivering device so as to deliver the analytical strip along a preset route fast and stably.

Yet another objective of the present invention is to provide an analytical strip reading apparatus comprising a delivering device for automatically delivering an analytical strip supported thereon into and out of a housing so as to avoid mutual contamination between a user and a specimen.

Yet another objective of the present invention is to provide an analytical strip reading apparatus comprising a reaction signal reader for simultaneously acquiring reaction signals emitted from a biochemical analytical strip or an immunological analytical strip.

Still another objective of the present invention is to provide an analytical strip reading apparatus comprising a reaction signal reader for separately acquiring reaction signals emitted from a biochemical analytical strip or an immunological analytical strip.

A further objective of the present invention is to provide an analytical strip reading apparatus comprising an output device for outputting an analysis result of an analytical strip or an ID barcode by which the analytical strip corresponds to a test subject's data.

A further objective of the present invention is to provide an analytical strip reading apparatus comprising an optical reader which is configured to also read anamnesis data of a test subject from whom a specimen to be analyzed is obtained, thereby further providing a function of data integration.

A further objective of the present invention is to provide an analytical strip reading apparatus comprising an optical reader which is freely detachable to facilitate operation by a user.

A further objective of the present invention is to provide an analytical strip for being used in an analytical strip reading apparatus, wherein the analytical strip has at least one reaction zone for presenting a reaction signal and at least one optically readable pattern with identification information of the analytical strip, wherein the identification information essentially comprises a type, a lot number and an expiration date of the analytical strip as well as reagent calibration data corresponding to the lot number, and wherein the reaction zone and the optically readable pattern are defined at different locations, respectively.

Therefore, a further objective of the present invention is to provide an analytical strip for use in an analytical strip reading apparatus, wherein the analytical strip reading apparatus is configured to read identification information contained in an optically readable pattern of the analytical strip, thereby enabling automatic comparison and verification of a type, a lot number and an expiration date of the analytical strip as well as reagent calibration data corresponding to the lot number. In consequence, the incorrect operation or improper analytical strips can be prevented to ensure the reliability of analysis results.

A further objective of the present invention is to provide an analytical strip for use in an analytical strip reading apparatus, wherein the analytical strip comprises at least one optically readable pattern with identification information of the analytical strip, in which the optically readable pattern can be a one-dimensional barcode or a two-dimensional barcode.

A further objective of the present invention is to provide an analytical strip for use in an analytical strip reading apparatus, wherein the analytical strip comprises at least one optically readable pattern with identification information of the analytical strip, in which the optically readable pattern can be read with visible light, ultraviolet light or infrared light.

The invention as well as a preferred mode of use, further objectives and advantages thereof will be best understood by referring to the following detailed description of illustrative embodiments in conjunction with the accompanying drawings.

DETAILED DESCRIPTION OF THE INVENTION

The present invention discloses an analytical strip reading apparatus in which the principles of biological detection and fundamental electromechanical mechanisms employed are well known to those of ordinary skill in the art. Therefore, a detailed description of such principles and mechanisms will be omitted herein for brevity. Besides, the drawings referred to herein are not drawn according to actual dimensions and need not be so because they are intended to demonstrate features of the present invention only schematically.

Figure 1A:
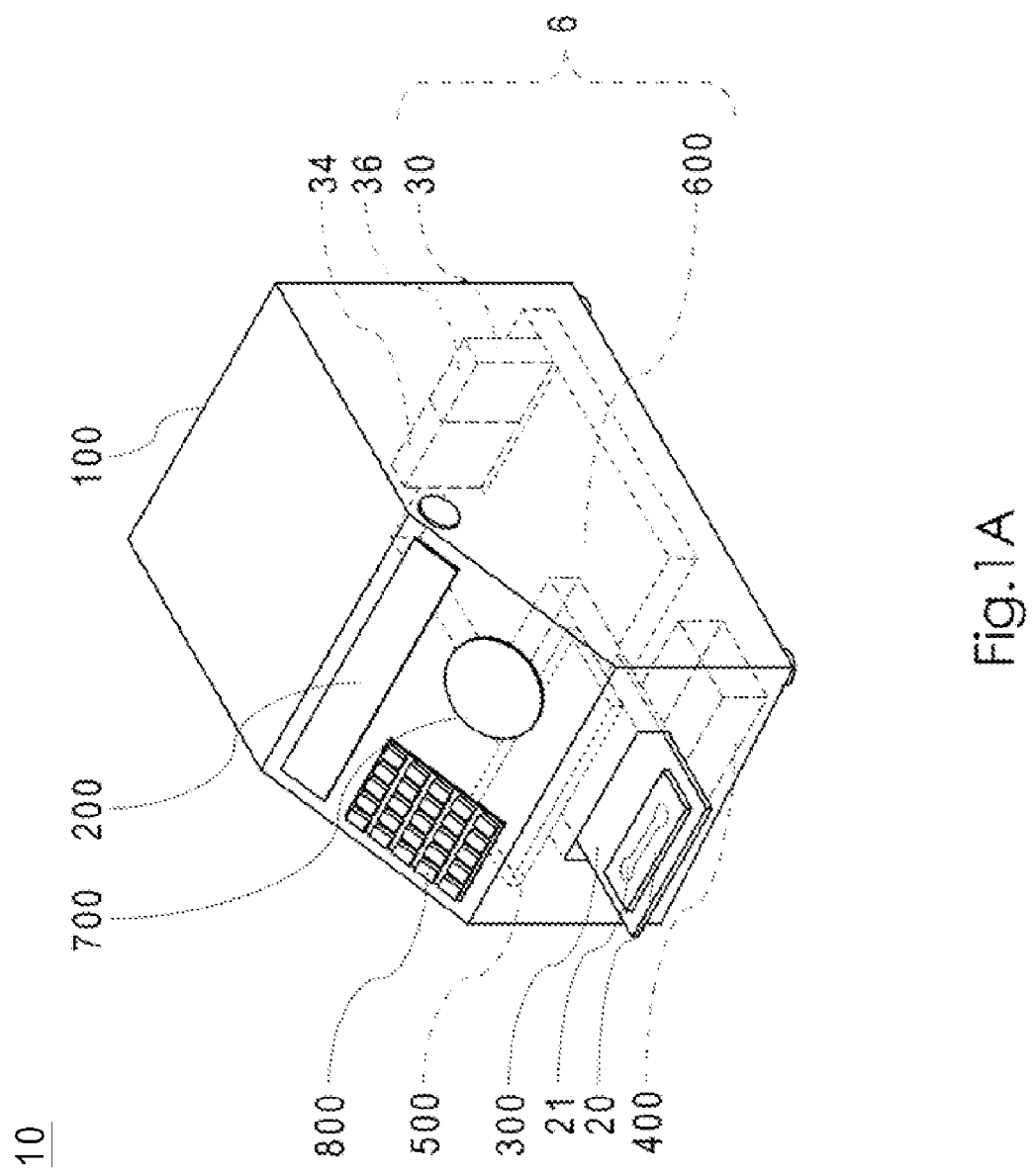
FIG. 1A is a perspective view of an analytical strip reading apparatus according to a first preferred embodiment of the present invention.

Please refer to FIG. 1A for an analytical strip reading apparatus 10 according to a first preferred embodiment of the present invention. The analytical strip reading apparatus 10, configured to read a reaction signal emitted from an analytical strip 20, includes a housing 100, a monitor 200, a delivering device 300, an optical reader 400, a reaction signal reader 500 and a control module 6. The analytical strip 20 comprises at least one reaction zone 21 for presenting the reaction signal, and at least one optically readable pattern 22 (as shown in FIG. 2B). The optically readable pattern 22 contains identification information of the analytical strip 20 and can be a one-dimensional barcode, a two-dimensional barcode or any optically readable patterns that are read with visible light, ultraviolet light or infrared light, so as to facilitate reading of the identification information of the analytical strip 20. The identification information includes a type, a lot number, and an expiration date of the analytical strip 20 as well as reagent calibration data corresponding to the lot number.

The monitor 200 is provided on the housing 100 for displaying an analysis result. The delivering device 300 is configured to support the analytical strip 20 and move the analytical strip horizontally along a preset route so as to deliver the analytical strip 20 automatically into or out of the housing 100. The delivering device 300 prevents unstable movement caused by manual operation and further provides a fast scanning function. According to the automatically delivering the analytical strip provided by the delivering device 300, it is not necessary for a user to place the analytical strip 20 into the analytical strip reading apparatus 10 manually. Hence, by excluding manual operation, mutual contamination between the analytical strip and the user's fingers can be avoided to ensure the reliability of the analysis result and protect the operator from accidentally contacting a biological specimen and thus being exposed to biological hazards. In addition, the aforesaid delivering device 300 also solves the problem of difficult removal of an analytical strip designed with improper dimensions.

Referring again to FIG. 1A, the optical reader 400 is located inside the housing 100 for reading the identification information in the optically readable pattern 22 of the analytical strip 20. The optically readable pattern 22 of the analytical strip 20 can be read in two ways. The first way is that the optical reader 400 reads the optically readable pattern 22 of the analytical strip 20 on the preset route of the delivering device 300 when the delivering device 300 moves the analytical strip 20 into the housing 100. The other way is that the optical reader 400 reads the optically readable pattern 22 of the analytical strip 20 when the analytical strip 20 is delivered by the delivering device 300 to the endpoint of the preset route. Preferably, the optical reader 400 and the reaction signal reader 500 are located on vertically opposite sides of the preset route of the delivering device 300.

Figure 1B:
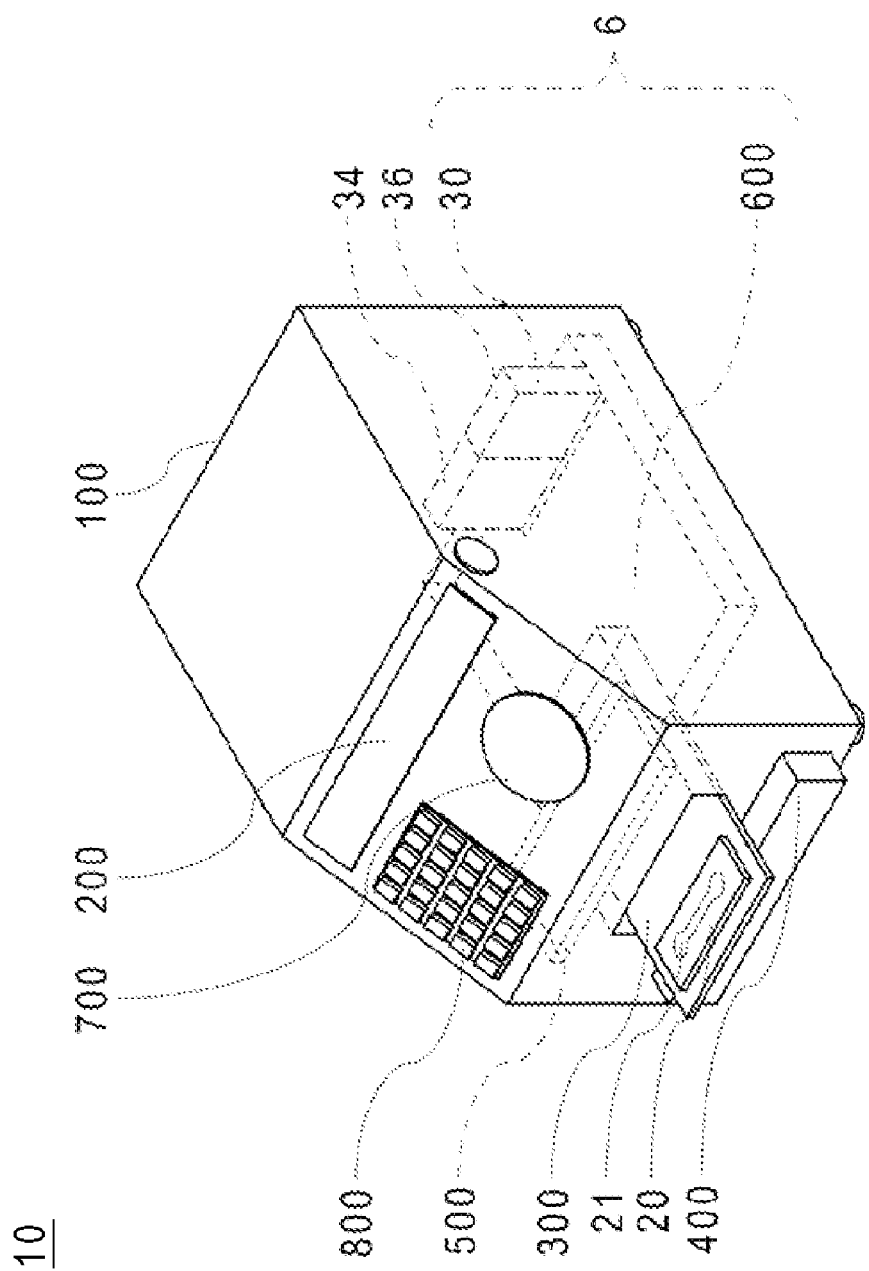
FIG. 1B is a perspective view of an analytical strip reading apparatus according to another mode of the first preferred embodiment of the present invention.

Referring now to FIG. 1B, the optical reader 400 may also be provided on a lateral side of the housing 100. This configuration allows the optical reader 400 to read the optically readable pattern 22 of the analytical strip 20 before the analytical strip 20 is placed in the delivering device 300. Besides, the optical reader 400 may also read an anamnesis barcode or ID barcode of a test subject corresponding to the analytical strip 20, thereby verifying whether or not the analytical strip 20 belongs to the test subject, as a way of recalibration, so that data integration can be done with respect to the test subject and the analytical strip 20. Moreover, the optical reader 400 may be freely detachable from the housing 100 to facilitate operation by the user. The optical reader 400, when detached, communicates with the analytical strip reading apparatus 10 via wireless or wire-based transmission.

By coding the type, the lot number and the expiration date of the analytical strip 20 as well as the reagent calibration data corresponding to the lot number into the optically readable pattern 22 of the analytical strip 20 and by using the analytical strip reading apparatus 10 to read such identification information automatically, inadvertent use of expired analytical strips can be effectively prevented. It also avoids waste of specimen and ensures the reliability of analysis results. It is possessed of a significant improvement over the prior art in which information related to the analytical strips is verified or input manually.

The reaction signal reader 500 is located inside the housing 100 for acquiring the reaction signal emitted from the reaction zone 21 of the analytical strip 20. The reaction signal may include a photoreaction signal or a electrochemical reaction signal. The reaction signal reader 500 acquires the reaction signal also in two ways. The first way is that the reaction signal reader 500 acquires the reaction signal when the delivering device 300 is delivering the analytical strip 20 into the housing 100 along the preset route. The other way is that the reaction signal reader 500 acquires the reaction signal after the delivering device 300 has delivered the analytical strip 20 to the endpoint of the preset route.

The control module 6 comprises a mother board 600 and a firmware device 30 attached to the mother board 600. The firmware device 30 includes a database sub-module 34 and a processing sub-module 36. The database sub-module 34 is configured for storing reaction signal data of analytical strips of various types, such as the liquid detection data required for performing a blood glucose test, a total cholesterol test, an uric acid test and so on. The processing sub-module 36 is configured for reading, according to the type of the analytical strip 20, the reaction signal data stored in the database sub-module 34 corresponding to the type of the analytical strip 20, as well as the reagent calibration data corresponding to the lot number of the analytical strip 20, and comparing the reaction signal emitted from the analytical strip 20 against the data and the information read, so as to come out the analysis result. Additionally, according to the expiration date of the analytical strip 20, the processing sub-module 36 may also stop the reaction signal reader 500 from reading, or allow the reaction signal reader 500 to read, the reaction signal emitted from the analytical strip 20.

For example, during a blood glucose test, the analytical strip 20 is placed into the analytical strip reading apparatus 10, so that the optical reader 400 reads the type of the analytical strip 20 to enable verification of the type as the appropriate one for the blood glucose test or otherwise. Meanwhile, the optical reader 400 also reads from the optically readable pattern 22 such identification information as the lot number and the expiration date of the analytical strip 20 for automatic comparison by the analytical strip reading apparatus 10. If the type and the expiration date of the analytical strip 20 are verified as correct, the reaction signal reader 500 will read the reaction signal emitted from the analytical strip 20. The reaction signal acquired by the reaction signal reader 500 from the analytical strip 20 will be transmitted, along with the reaction signal data regarding the blood glucose test provided by the database sub-module 34 when the analytical strip reading apparatus 10 verifies the analytical strip 20 as the correct one for the blood glucose test, in combination with the reagent calibration data contained in optically readable pattern 22 of the analytical strip 20, to the processing sub-module 36 for operation, so as to come out a blood glucose analysis result.

Figure 1C:
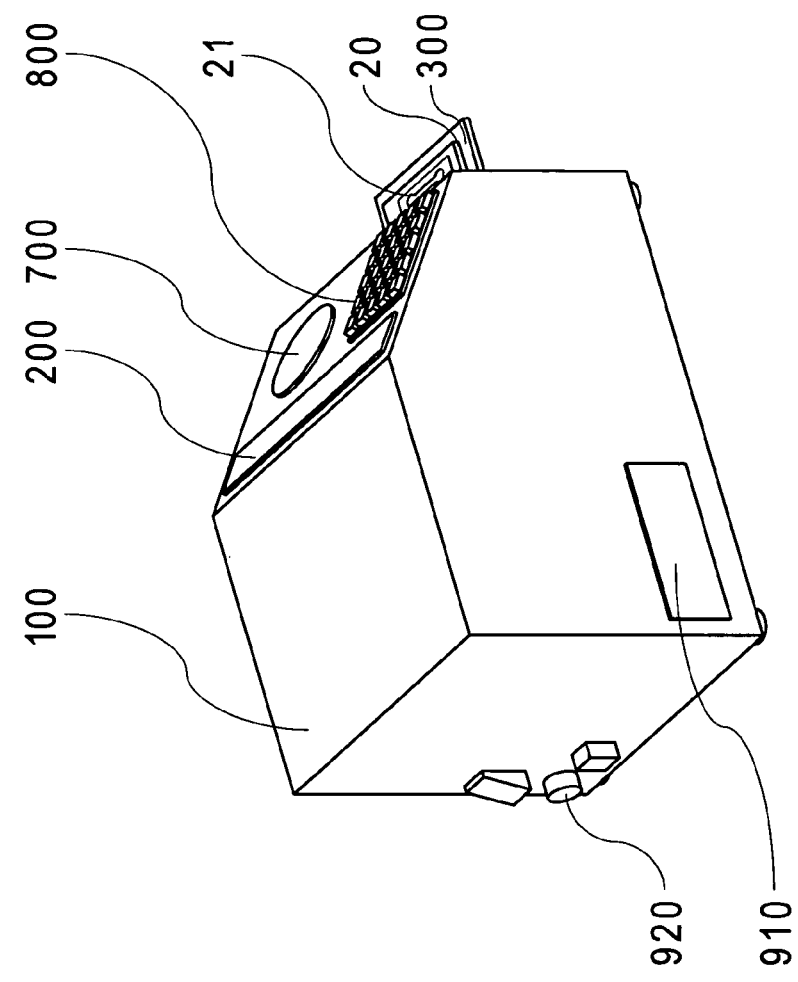
FIG. 1C is a perspective view of the analytical strip reading apparatus according to the first preferred embodiment of the present invention as observed from another viewing angle.

Referring to FIG. 1C, the analytical strip reading apparatus 10 further includes an output device, such as a printer output port 910 and a USB output port 920, for outputting the analysis result. The analytical strip reading apparatus 10 may also be provided with a Bluetooth (IEEE 802.15) output port (not shown) as appropriate.

Moreover, the analytical strip reading apparatus 10 further includes an operation switch 700 which must be turned on first before the delivering device 300 delivering the analytical strip 20 along the preset route. The operation switch 700 further provides a terminating function such that operation of the analytical strip reading apparatus 10 is terminated by operating the operation switch 700.

The analytical strip reading apparatus 10 further includes an input keyboard 800. In the event that the analytical strip 20 does not contain information readable by the optical reader 400 or the optical reader 400 is damaged, the type, the lot number and the expiration date of the analytical strip 20 as well as the reagent calibration data corresponding to the lot number can be input manually via the input keyboard 800. The user may also use the input keyboard 800 to manually input the anamnesis barcode or ID barcode of the test subject into the analytical strip reading apparatus 10. The manually inputted information can also be outputted via the output device such as the printer output port 910 and/or the USB output port 920.

Figure 2A:
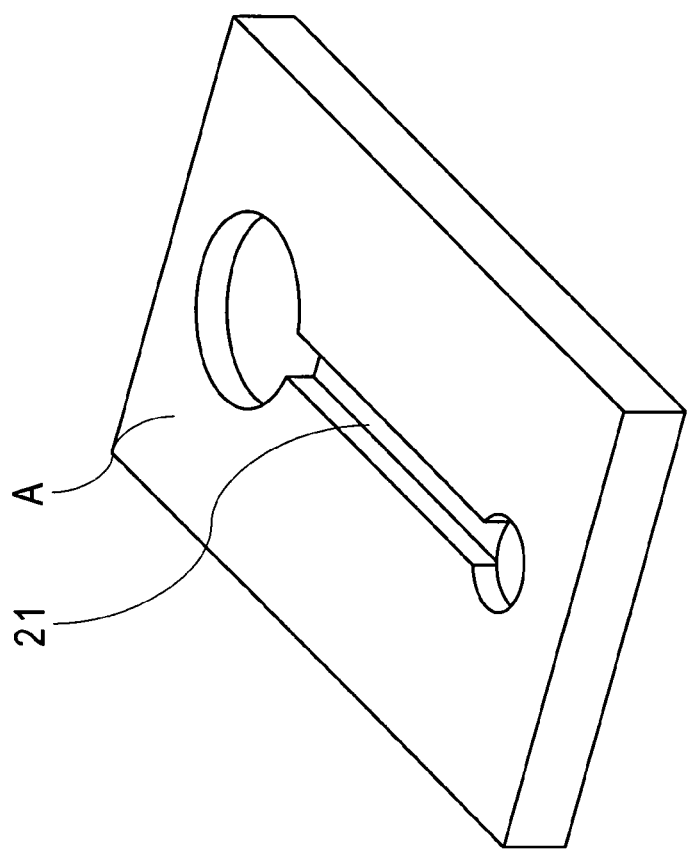
FIG. 2A is a perspective view of an analytical strip according to a second preferred embodiment of the present invention, wherein the analytical strip has a surface A defined with a reaction zone thereon.
Figure 2B:
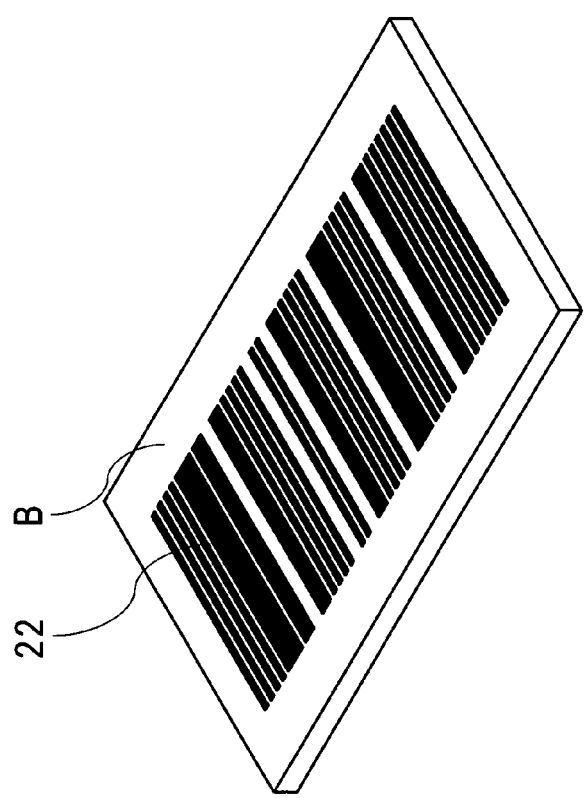
FIG. 2B is a perspective view of the analytical strip according to the second preferred embodiment of the present invention, wherein the analytical strip has a surface B facing away from the surface A and defined with an optically readable pattern thereon.

Reference is now made to FIGS. 2A and 2B, wherein a second preferred embodiment of the present invention, namely an analytical strip 20 for being used in the analytical strip reading apparatus 10, is shown. The analytical strip 20 has at least one reaction zone 21 for presenting a reaction signal, and at least one optically readable pattern 22. The optically readable pattern 22 contains identification information of the analytical strip 20, such as a type, a lot number and an expiration date of the analytical strip as well as reagent calibration data corresponding to the lot number. In a preferred configuration of the present invention, the reaction zone 21 and the optically readable pattern 22 are defined on two opposite surfaces of the analytical strip 20, respectively, wherein the two opposite surfaces of the analytical strips 20 are not in contact with each other. For example, as shown in FIGS. 2A and 2B, the reaction zone 21 is defined on a surface A of the analytical strip 20, and the optically readable pattern 22 is defined on an opposite surface B facing away from the surface A. Other features of the analytical strip 20 are identical to those of its counterpart in the first preferred embodiment of the present invention.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the spirit of the present invention should be encompassed by the appended claims.

What is claimed is:

1. An analytical strip reading apparatus for acquiring reaction signals emitted from reaction zones on an analytical strip by performing an assay for analytes, the analytical strip having at least one reaction zone for presenting the reaction signal and at least one optically readable pattern with identification information of the analytical strip, in which the identification information essentially comprises a type, a lot number and an expiration date of the analytical strip as well as reagent calibration data corresponding to the lot number, the analytical strip reading apparatus essentially comprising a housing and a monitor provided on the housing, the analytical strip reading apparatus being characterized by further comprising:
a delivering device for supporting and moving the analytical strip along a preset route so as to deliver the analytical strip into or out of the housing;
an optical reader for reading the identification information contained in the optically readable pattern of the analytical strip;
a reaction signal reader located inside the housing for acquiring the reaction signal emitted from the analytical strip; and
a control module comprising a mother board and a firmware device attached to said mother board, said firmware device including:
a database sub-module for storing algorithms corresponding to various types of analytical strips; and
a processing sub-module for retrieving the algorithm stored in the database sub-module corresponding to the type of the analytical strip, combining the reagent calibration data corresponding to the lot number of the analytical strip, and comparing the reaction signal from the analytical strip, so as to come out an analysis result of the assay.

2. The analytical strip reading apparatus of claim 1, wherein the reaction signal reader acquires the reaction signal emitted from the analytical strip on the preset route of the delivering device while the analytical strip is moved into the housing.

3. The analytical strip reading apparatus of claim 1, wherein the reaction signal reader acquires the reaction signal emitted from the analytical strip after the analytical strip is moved to an endpoint of the preset route.

4. The analytical strip reading apparatus of claim 1, wherein the delivering device moves the analytical strip horizontally.

5. The analytical strip reading apparatus of claim 1, wherein the optical reader is located inside the housing and reads the optically readable pattern of the analytical strip while the analytical strip is moved along the preset route.

6. The analytical strip reading apparatus of claim 1, wherein the optical reader is located inside the housing and reads the optically readable pattern of the analytical strip after the analytical strip is moved to an endpoint of the preset route.

7. The analytical strip reading apparatus of claim 1, wherein the optical reader and the reaction signal reader are located on opposite sides of the preset route.

8. The analytical strip reading apparatus of claim 1, wherein the analysis result is displayed on the monitor, and the analytical strip reading apparatus further comprises an input keyboard for enabling manual input of the identification information of the optically readable pattern of the analytical strip.

9. The analytical strip reading apparatus of claim 1, wherein the processing sub-module of the control module stops or allows the reaction signal reader acquiring the reaction signal emitted from the analytical strip according to the expiration date of the analytical strip.

10. The analytical strip reading apparatus of claim 1, wherein the optically readable pattern is selected from the group consisting of a one-dimensional barcode and a two-dimensional barcode.

11. The analytical strip reading apparatus of claim 1, wherein the optically readable pattern is read with the light selected from the group consisting of visible light, ultraviolet light, and infrared light.

12. The analytical strip reading apparatus of claim 1, wherein the reaction signal is selected from the group consisting of a photoreaction signal and an electrochemical reaction signal.

13. The analytical strip reading apparatus of claim 1, wherein the optical reader is provided on a lateral side of the housing and reads the optically readable pattern of the analytical strip before the analytical strip is moved into the housing.

14. The analytical strip reading apparatus of claim 13, wherein the optical reader further reads an anamnesis barcode or an ID barcode of a test subject corresponding to the analytical strip, so as to perform data integration with respect to the test subject and the analytical strip.

15. The analytical strip reading apparatus of claim 1, further comprising an output device for outputting the analysis result of the analytical strip.

16. The analytical strip reading apparatus of claim 15, wherein the output device is selected from the group consisting of a printer output port, a USB output port and a Bluetooth (IEEE 802.15) output port.

17. An analytical strip for being used in an analytical strip reading apparatus, wherein the analytical strip reading apparatus is used for acquiring reaction signals emitted from reaction zones on the analytical strip by performing an assay for analytes, the analytical strip reading apparatus essentially comprising a housing and a monitor provided on the housing, the analytical strip reading apparatus further comprising:
a delivering device for supporting and moving the analytical strip along a preset route so as to deliver the analytical strip into or out of the housing;
an optical reader for reading the identification information contained in the optically readable pattern of the analytical strip;
a reaction signal reader located inside the housing for acquiring the reaction signal emitted from the analytical strip; and
a control module comprising a mother board and a firmware device attached to said mother board, said firmware device including:
a database sub-module for storing algorithms corresponding to various types of analytical strips; and
a processing sub-module for retrieving the algorithm stored in the database sub-module corresponding to the type of the analytical strip, combining the reagent calibration data corresponding to the lot number of the analytical strip, and comparing the reaction signal from the analytical strip, so as to come out an analysis result of the assay, the analytical strip being characterized by comprising:
at least one reaction zone for presenting at least one reaction signal; and
at least one optically readable pattern with identification information of the analytical strip, wherein the identification information essentially comprises a type, a lot number and an expiration date of the analytical strip as well as reagent calibration data corresponding to the lot number, and in which said at least one reaction zone and said at least one optically readable pattern are defined at different locations.

18. An analytical strip for being used in an analytical strip reading apparatus, wherein the analytical strip reading apparatus is used for acquiring reaction signals emitted from reaction zones on the analytical strip by performing an assay for analytes, the analytical strip reading apparatus essentially comprising a housing and a monitor provided on the housing, the analytical strip reading apparatus further comprising:
  a delivering device for supporting and moving the analytical strip along a preset route so as to deliver the analytical strip into or out of the housing;
  an optical reader for reading the identification information contained in the optically readable pattern of the analytical strip;
  a reaction signal reader located inside the housing for acquiring the reaction signal emitted from the analytical strip; and
  a control module comprising a mother board and a firmware device attached to said mother board, said firmware device including:
    a database sub-module for storing algorithms corresponding to various types of analytical strips; and
    a processing sub-module for retrieving the algorithm stored in the database sub-module corresponding to the type of the analytical strip, combining the reagent calibration data corresponding to the lot number of the analytical strip, and comparing the reaction signal from the analytical strip, so as to come out an analysis result of the assay, the analytical strip being characterized by comprising:
  at least one reaction zone for presenting at least one reaction signal;
  at least one optically readable pattern with identification information of the analytical strip, wherein the identification information essentially comprises a type, a lot number and an expiration date of the analytical strip as well as reagent calibration data corresponding to the lot number; and
  two opposite and non-contact surfaces, the reaction zone and the optically readable pattern being defined on said surfaces, respectively.

* * * * *